United States Patent
Cho et al.

(10) Patent No.: US 7,074,602 B2
(45) Date of Patent: Jul. 11, 2006

(54) METHOD FOR PRODUCING L-THREONINE

(75) Inventors: Jae Yong Cho, Yongin (KR); Byoung Choon Lee, Seoul (KR); Dae Cheol Kim, Suwon (KR); Jin Ho Lee, Icheon (KR); Young Hoon Park, Seongnam (KR)

(73) Assignee: CJ Corporation (KR)

( * ) Notice: Subject to any disclaimer, the term of this patent is extended or adjusted under 35 U.S.C. 154(b) by 0 days.

(21) Appl. No.: 10/916,804

(22) Filed: Aug. 12, 2004

(65) Prior Publication Data

US 2005/0054076 A1    Mar. 10, 2005

(30) Foreign Application Priority Data

Sep. 6, 2003    (KR) ..................... 10-2003-0062423

(51) Int. Cl.
*C12N 1/20* (2006.01)
*G12P 13/12* (2006.01)
*C07H 21/02* (2006.01)
*C07H 21/04* (2006.01)

(52) U.S. Cl. ............... 435/115; 435/108; 435/252.33; 435/282.8; 536/23.1; 536/24.1

(58) Field of Classification Search ........... 435/252.33, 435/108, 115, 282.8; 536/23.1, 24.1
See application file for complete search history.

(56) References Cited

U.S. PATENT DOCUMENTS

| 5,538,873 A | 7/1996 | Debabov et al. ............. 435/115 |
| 5,939,307 A | 8/1999 | Wang et al. ............ 435/252.33 |

FOREIGN PATENT DOCUMENTS

| EP | 0 593 792 A1 | 4/1994 |
| JP | 01-289493 | 11/1989 |
| JP | 02-219582 | 9/1990 |
| KR | 1992-0008365 | 9/1992 |
| WO | WO 98/04715 | 2/1998 |
| WO | WO 02/064808 A1 | 8/2002 |

OTHER PUBLICATIONS

"L-Threonine production by L-asparatate-and L-hormoserine-resistant mutant of *Escherichia coli*", Appl Microbiol Biotechnol (1988) 29:550-553; authors: Satoru Furukawa, Akio Ozaki, and Toshihide Nakanishi.

"A new efficient gene disruption cassette for repeated use in budding yeast", Nuclei Acids Research, (1996) vol. 24, No. 13 2519-2524; Oxford University Press; Authors: Ulrich Guldener, Susanne Heck, Thomas Fiedler, Jens Beinhauer and Johannes H. Hegemann.

"Essential Features of Plasmids". Plasmid Vectors; pp. 1.3-1.11.

"Transfer Denatured RNA to Nitrocellulose Filters". Extraction, Purification, and Analysis of Messenger RNA from Eukaryotic Cells; pp. 7.46-7.48.

Mechanism of Repression of Methionine Biosynthesis in *Escherichia coli* II. The effect of *metJ* Mutations on the Free Amino Acid Pool; Authors: Michael T. Clandinin and Asad Ahmed; Molec. gen. Genet. 123, 325-331 (1973); Springer-Verlag; XP009048031.

European Search Report; Application No. EP 04 35 6152; Date of Completion: May 23, 2005.

*Primary Examiner*—Rebecca E. Prouty
*Assistant Examiner*—Malgorzata Walicka
(74) *Attorney, Agent, or Firm*—Cantor Colburn LLP

(57) ABSTRACT

An L-threonine-producing *Escherichia coli* strain and a method for producing the same are provided. The *Escherichia coli* strain contains chromosomal DNA with inactivated metJ gene. Therefore, expression repression of threonine biosynthesis genes by a metJ gene product is prevented, thereby producing a high concentration of threonine. Further, a high concentration of L-threonine can be produced in high yield using the method.

4 Claims, 4 Drawing Sheets

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
agttccctgg gctttgtcg                                              19

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gctaggcctg ataagcgtag c                                           21

METHOD FOR PRODUCING L-THREONINE

BACKGROUND OF THE INVENTION

This application claims priority from Korean Patent Application No. 2003-62423 filed on Sep. 6, 2003, in the Korean Intellectual Property Office, the disclosures of which are incorporated herein in their entireties by reference.

1. Field of the Invention

The present invention relates to an L-threonine-producing *Escherichia coli* strain, and a method for producing L-threonine using the *Escherichia coli* strain.

2. Description of the Related Art

L-threonine is an essential amino acid and is widely used as a feed or food additive. In addition, L-threonine is used as a medical solution or a raw material for a drug synthesis.

L-threonine is produced by a fermentation process using a mutant strain derived from a wild-type strain of *Escherichia coli* (*E.coli*), *Corynebacteria* sp., *Serratia* sp., or *Providencia* sp. Examples of the mutant strain include an amino acid analogue- or drug-resistant mutant strain, and a diaminopimeric acid, a methionine, a lysine, or an isoleucine auxotrophic mutant strain that has an amino acid analogue- or drug-resistance. These mutant strains are disclosed in Japanese Patent Laid-Open Publication No. Hei. 2-219582; *Appl. Microbiol. Biotechnol.*, 29. 550–553 (1988); Korean Patent Laid-Open Publication No. 1992-12423; and the like. Korean Patent Laid-Open Publication No. 1992-12423 discloses an L-threonine-producing *E. coli* TF4076 (KFCC 10718). The *E. coli* TF4076 is a methionine auxotrophic strain, and has a resistance to a threonine analogue (AHV: α-amino-β-hydroxy valeric acid), a lysine analogue (AEC: S-(2-aminoethyl)-L-cysteine), an isoleucine analogue (α-aminobutyric acid), and a methionine analogue (ethionine).

A fermentation process using a recombinant strain can also be used in production of L-threonine. For example, Japanese Patent Laid-Open Publication No. Hei. 5-10076 discloses a method for producing threonine in large scale using a recombinant strain of *Serratia* sp. containing a DNA fragment with genetic information of aspartokinase, homoserine kinase, homoserine dehydrogenase, and threonine synthase. In addition, a method of increasing the production of L-threonine using a gene derived from a strain of *Providencia* sp. resistant to antagonist of methionine metabolism is disclosed in Japanese Patent Laid-Open Publication No. Hei. 1-289493.

Meanwhile, the expression of a gene in a microorganism can be enhanced by increasing the copy number of the gene contained in the microorganism. For this, a plasmid that gives a greater copy number to a microorganism is used [Sambrook et al., *Molecular Cloning*, 2th, 1989, 1.3–1.5]. That is, the copy number of a plasmid in a microorganism is increased by inserting a target gene into the plasmid and then transforming the microorganism with the obtained recombinant plasmid. Attempts have been made to enhance the productivity of threonine using this method and a partial success was reported (U.S. Pat. No. 5,538,873). However, this technology using plasmid induces excessive expression of a specific gene in most cases, thereby imposing a heavy burden on a host microorganism. Furthermore, a plasmid loss during culture may be caused, thereby decreasing plasmid stability.

In order to solve these problems, addition of an antibiotic into a culture and using a plasmid containing an expression regulatory sequences were introduced by Sambrook et al. [*Molecular Cloning*, 2th, 1989, 1.5–1.6, 1.9–1.11]. In the case of using a plasmid containing an expression regulatory sequences, during the growth phase, a host microorganism is cultured so that no expression is induced, thereby decreasing a burden on the host microorganism. On the other hand, after the sufficient growth of the host microorganism, temporary expression is induced, thereby releasing a gene product. However, most of these plasmids containing an expression regulatory sequences can be used only when a final gene product is a protein. In a case where a gene product is a primary metabolite that is closely associated with the growth of microorganisms, expression of a target gene must be induced during the growth phase. Otherwise, it is difficult to anticipate the accumulation of the primary metabolite. Since threonine belongs to a primary metabolite, the above case is also applied to threonine.

As a method for producing threonine without these problems, inserting a threonine biosynthesis gene into chromosomal DNA is disclosed in U.S. Pat. No. 5,939,307. Further, there is disclosed a method for producing threonine by regulation of expression of threonine operon, for example, replacing a promoter of the threonine operon with tac promoter (WO 98/04715) or replacing an expression regulatory region of the threonine operon with cl repressor and PR promoter of *E. coli* λ phage (EP 0593792). In this case, however, since a gene on a chromosome is substituted by corresponding gene containing an inducible promoter, it is difficult to greatly increase the expression of threonine operon genes.

In this regard, while searching for solutions to the problems of the above-described conventional L-threonine production methods, considering the fact that metJ gene represses the expression of metL gene, one of genes regulating the biosynthesis pathway of threonine and methionine, the present inventors found that an *E. coli* strain containing chromosomal DNA with inactivated metJ gene can produce a high yield of L-threonine, and then completed the present invention.

SUMMARY OF THE INVENTION

Therefore, the present invention provides an *Escherichia coli* (*E. coli*) strain capable of producing L-threonine in high yield.

The present invention also provides a method for producing L-threonine using the *E coli*.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention provides a L-threonine-producing *Escherichia coli* (*E. coli*) strain that contains chromosomal DNA with inactivated metJ gene.

As used herein, the term "inactivated metJ gene" or similar expressions indicate that no or little expression of the metJ gene is induced, or even if the expression is possible, the metJ gene has no or little activity. The inactivation of the metJ gene may be induced by mutation. Examples of the mutation include insertion, deletion, and inversion. Preferably, the metJ gene is inactivated by insertion of a sequence. For this, after deletion of all or part of the metJ gene, an antibiotic resistance gene (referred to as "antibiotic marker", hereinafter) may be inserted into the deletion site. By doing so, a specific antibiotic can be advantageously used as a selection agent when a strain containing the inactivated metJ gene is selected to be cultured. The antibiotic marker may be $kan^r$, $tet^r$, or $amp^r$, but is not limited thereto.

The metJ gene may be inactivated by mutation induced by exposure to chemicals or radiation. Alternatively, only the metJ gene may be specifically inactivated using genetic recombination. According to an example of the latter, a DNA fragment containing a part of a nucleotide sequence homologous to the metJ gene and containing the inactivated metJ gene is inserted into *E. coli* host strains to induce homologous recombination, and *E. coli* strains containing the inactivated metJ gene are then selected. The DNA fragment may be the ΔmetJ::loxpKan shown in FIG. 2.

Figure 4:
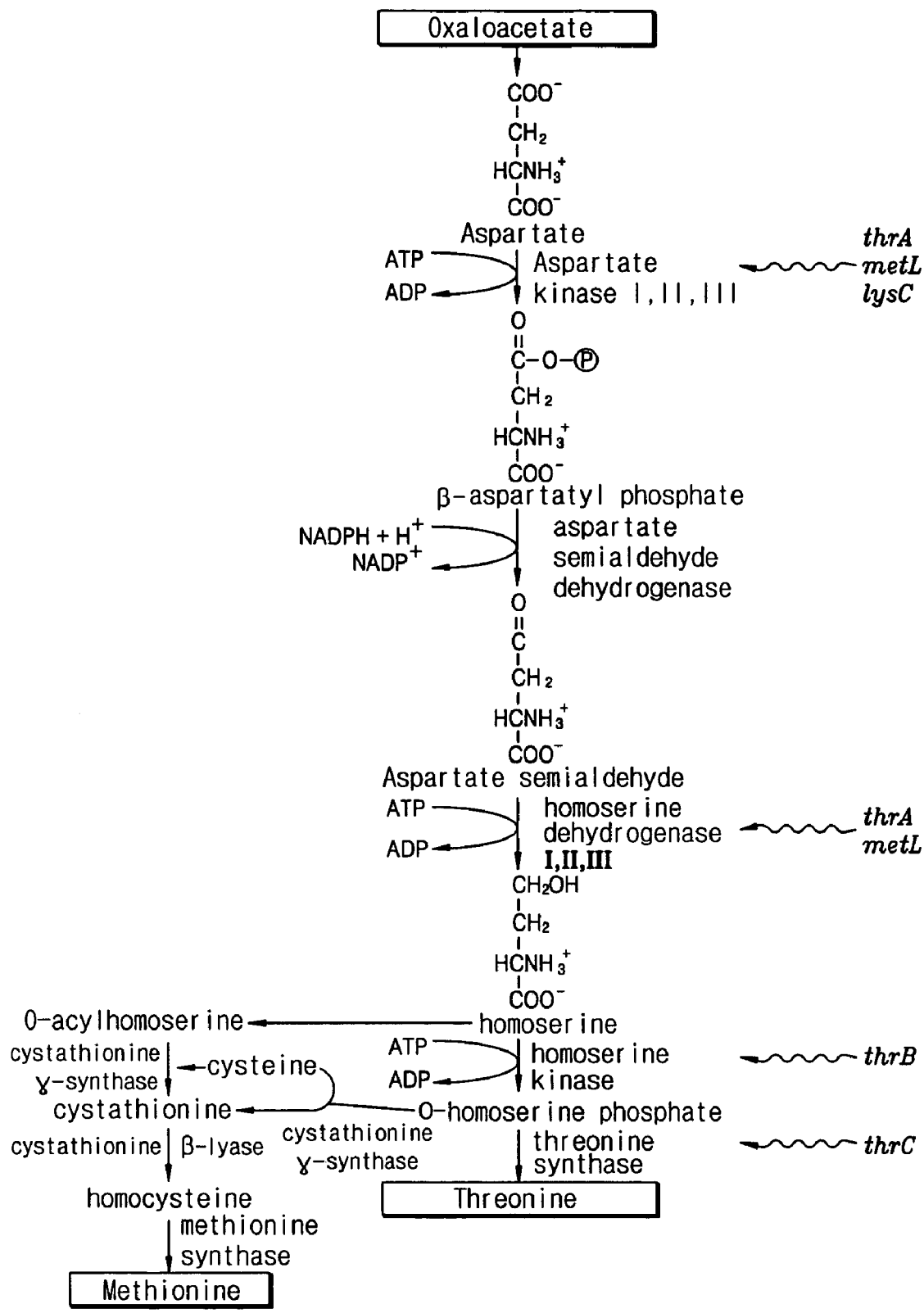
FIG. 4 is a flow diagram of the biosynthesis pathway of methionine and threonine.

The metJ gene encodes metJ protein repressing the expression of metL gene associated with the biosynthesis of threonine and methionine. The metJ protein is a protein that regulates the biosynthesis pathway of methionine in *E. coli*. The metJ protein represses the expression of the metL gene associated with threonine biosynthesis, together with its corepressor, S-adenosylmethionine (SAM). Referring to FIG. 4, the thrA gene, the metL gene, and the lysC gene encode aspartate kinase I, II, and III, respectively. Also, the thrA gene and the metL gene encode homoserine dehydrogenase I and II, respectively. In this regard, in the *E. coli* strain containing inactivated metJ gene according to the present invention, the expression of the metL gene is deregulated. That is, the expression of the metL gene is induced, thereby facilitating threonine biosynthesis.

The *E. coli* strain according to the present invention has threonine production capability. Preferably, the *E. coli* strain has resistance to a threonine analogue, a lysine analogue, an isoleucine analogue, and a methionine analogue. Also, the *E. coli* strain may further contain a threonine biosynthesis gene such as phosphoenolpyruvate carboxylase gene (referred to as "ppc gene", hereinafter). *E. coli* FTR1221 (accession number: KCCM-10392) is preferred.

The *E. coli* FTR1221 (accession number: KCCM-10392) is a resultant of inactivation of metJ gene in *E. coli* pGmTN-PPC12 (accession number: KCCM-10236) containing chromosomal DNA with duplicate copies of ppc genes and threonine operons. The *E. coli* pGmTN-PPC12 (accession number: KCCM-10236) is a resultant of inserting, into *E. coli* TF4076 (accession number: KFCC-10718) (Korean Patent Laid-Open Publication No. 92-12423) as a L-threonine-producing strain, the ppc gene and the threonine operon obtained by PCR from the chromosomal DNA of the *E. coli* TF4076. Therefore, in the *E. coli* pGmTN-PPC12, the gene for the ppc that is an enzyme converting phophoenolpyruvate (PEP) to oxaloacetate which is a precursor for threonine biosynthesis, and genes (thrA, thrB, and thrC) participating in the threonine biosynthesis pathway for producing threonine from the oxaloacetate are expressed at a high level. As a result, the *E. coli* pGmTN-PPC12 is characterized by its capability of producing enhanced L-threonine. The *E. coli* pGmTN-PPC12 was deposited in the Korean Culture Center of Microorganisms on Dec. 29, 2000 (accession number: KCCM-1 0236).

The present invention provides a method for producing L-threonine, the method including:

(a) culturing a L-threonine-producing *E. coli* strain that contains chromosomal DNA with inactivated metJ gene; and (b) recovering L-threonine from the culture.

In step (a), the culturing may be carried out in a common *E. coli* culture medium and condition well known to ordinary persons skilled in the art. The culturing may be carried out in various manners depending on a used strain and a culture scale.

In step (b), any recovering method known to ordinary persons skilled in the art may be used. For example, *E. coli* strains are removed from the culture, followed by ion exchange chromatography and crystallization, but is not limited thereto.

The L-threonine production method according to the present invention will now be described in more detail by way of examples.

1. Construction of Recombinant Plasmid

Chromosomal DNA is extracted from a threonine-producing strain to be used in construction of a recombinant plasmid pT7Blue/metJ containing a metJ gene fragment. Although there is no particular limitation to a cloning vector that can be used, it is preferable to use a pT7Blue cloning vector.

A loxP site-containing kanamycin resistance gene fragment is inserted into the recombinant plasmid pT7Blue/metJ to obtain a recombinant plasmid pT7ΔmetJ::loxpKan. As a result, the recombinant plasmid pT7ΔmetJ::loxpKan contains inactivated metJ gene.

Figure 3:
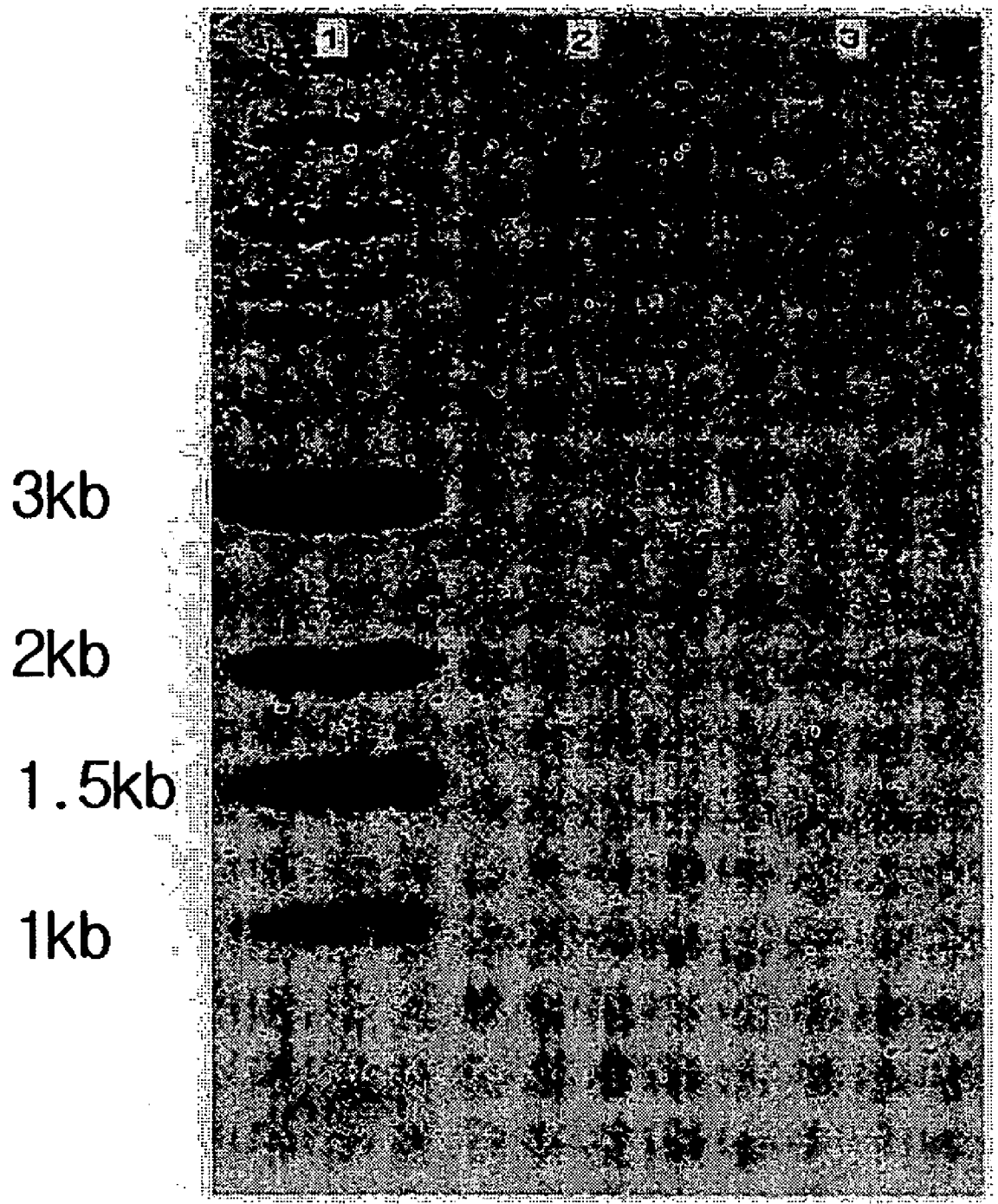
FIG. 3 is a southern blotting analysis result for a size marker (lane 1), parent strain pGmTN-PPC12 (lane 2), and *E. coli* FTR1221 (accession number KCCM-10392) (lane 3), using a FLA-5000 image process system (FUJIFILM)

2. Insertion of DNA Fragment Containing Inactivated metJ Gene into Strain and Strain Selection An *E. coli* strain is transformed with the recombinant plasmid pT7ΔmetJ::loxpKan and a plasmid DNA is extracted from the transformed *E. coli* strain. The plasmid DNA is digested with a restriction enzyme, followed by electrophoresis, to obtain a DNA fragment, ΔmetJ::loxpKan (FIG. 3).

The ΔmetJ::loxpKan DNA fragment is transformed into a threonine-producing strain. As a result, native metJ gene is replaced with the ΔmetJ::loxpKan DNA fragment by homologous recombination.

The transformant thus obtained is smeared onto a kanamycin-containing solid medium to select colonies. Consequently, recombinant strains containing inactivated metJ gene can be selected from the colonies.

The recombinant strains thus selected stably maintain the inactivated state of the metJ gene even when their growth continues, as well as having excellent threonine production capability, relative to the parent strain.

Hereinafter, the present invention will be described more specifically by Examples. However, the following Examples are provided only for illustrations and thus the present invention is not limited to or by them.

EXAMPLE 1

Construction of Recombinant Plasmid and Inactivation of metJ Gene Using the Recombinant Plasmid Chromosomal DNAs were extracted from threonine-producing strains, pGmTN-PPC12 (accession number: KCCM-10236) using a QIAGEN Genomic-tip system. About 700 bp fragments containing the open reading frames (ORFs) of metJ genes were amplified by PCR using the chromosomal DNAs as templates. Primers for the amplification were those as set forth in SEQ ID NO: 1 and SEQ ID NO: 2, and PCR premix (Bioneer Co.) was used as a reaction mixture for the PCR. The PCR reaction was performed at 94° C. for 30 seconds for denaturation, 55° C. for 30 seconds for annealing, and 72° C. for 1 minute and 30 seconds for extension for 30 cycles.

Figure 1:
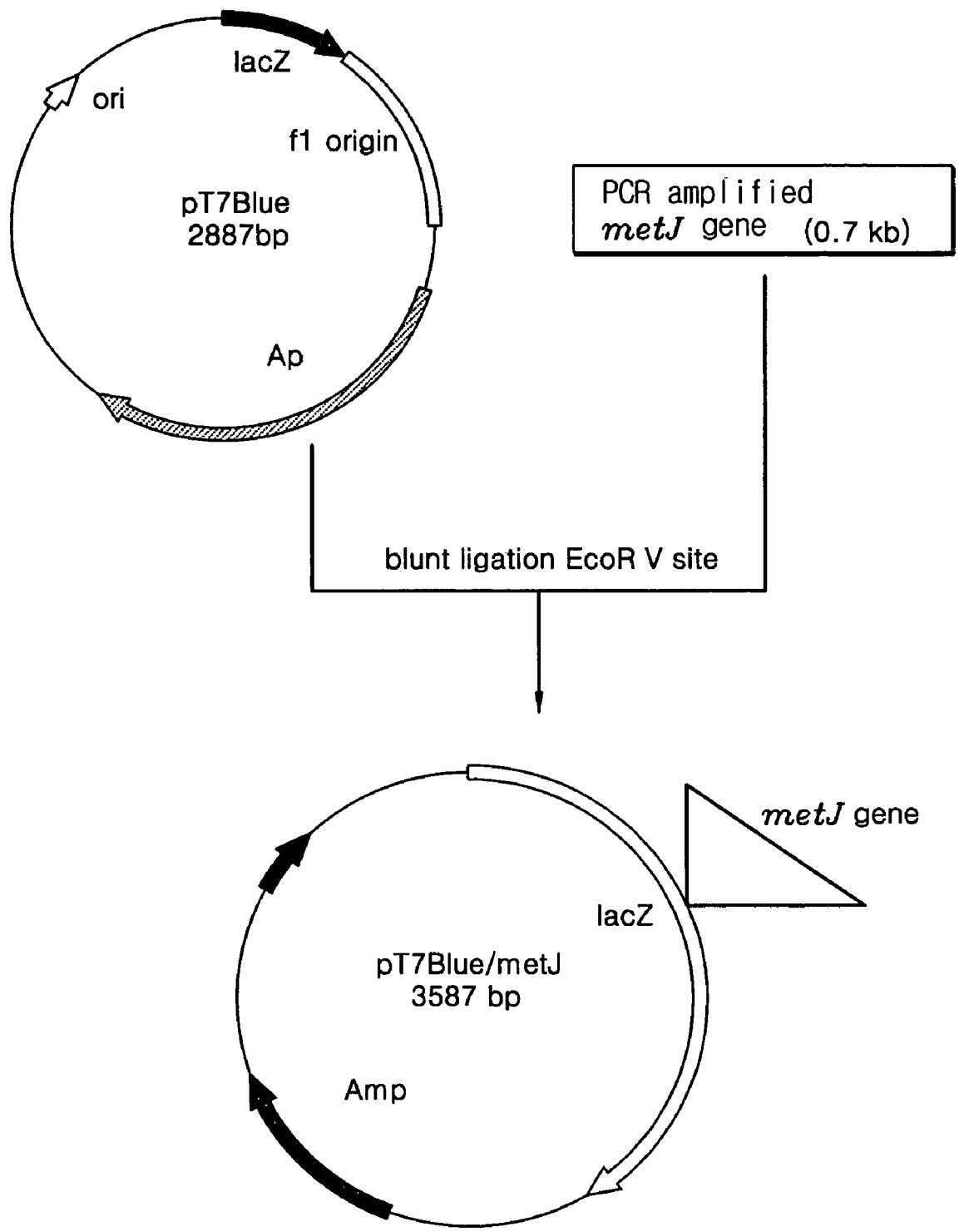
FIG. 1 is a scheme of the construction of a recombinant plasmid pT7Blue/metJ.

After the PCR products were size-fractionated by 0.1% agarose gel electrophoresis, bands containing DNA fragments of desired sizes were purified. The DNA fragments were ligated with pT7Blue cloning vectors (Novagen Co.) at 16° C. overnight. As a result, recombinant plasmids, pT7Blue/metJ were obtained (FIG. 1). After E. coli NM522 was transformed with the pT7Blue/metJ, the obtained transformants were smeared onto solid media (50 mg/L) and cultured at 37° C. overnight.

Figure 2:
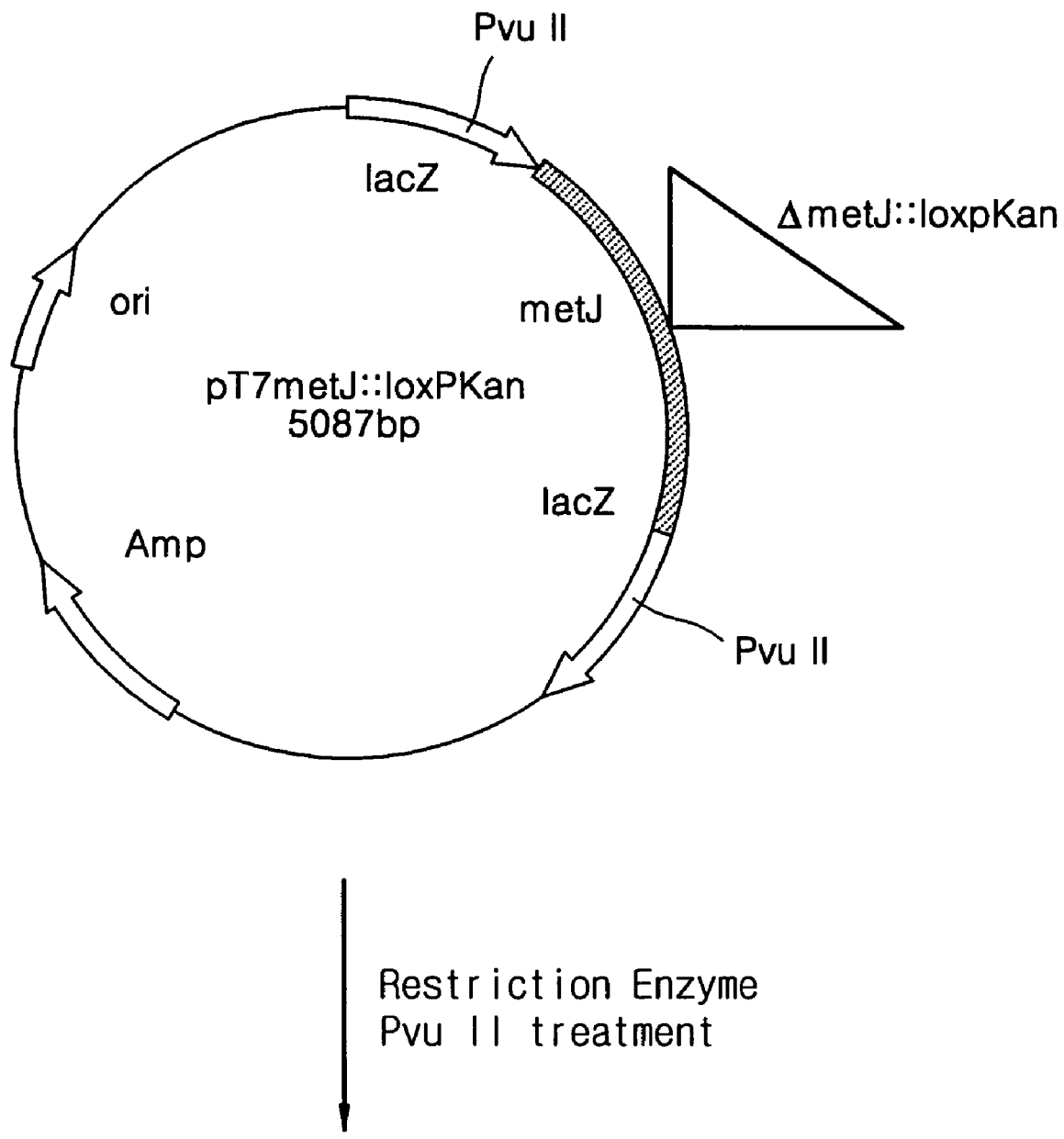
FIG. 2 is a scheme of the construction of a recombinant plasmid pT7ΔmetJ::loxpKan and a ΔmetJ::loxpKan DNA fragment.

Colonies grown on the solid media were inoculated by a toothpick onto 3 mL of liquid media containing carbenicillin and cultured overnight. Then, plasmid DNAs were isolated using a QIAGEN mini prep kit and their sizes were determined. Also, the plasmid DNAs were digested with restriction enzyme Mlu I to determine the presence of cloned metJ gene fragments. The plasmid DNAs were identified as pT7Blue/metJ DNAs. The pT7Blue/metJ DNAs were digested with restriction enzyme Mlu I and bands of 3.6 kb were resolved on 0.8% agarose gel. DNA fragments contained in the bands were digested with Klenow enzyme to obtain blunt-ended DNA fragments. On the other hand, plasmids pUG6 [Ulrich et al., *Nucleic Acids Research,* 1996, 24, pp. 2519–2524] were digested with restriction enzymes Hinc II and EcoR V to obtain loxP site-containing kanamycin resistance gene fragments (about 1.7 kb). The blunt-ended DNA fragments were ligated with the loxP site-containing kanamycin resistance gene fragments to obtain recombinant plasmids, pT7ΔmetJ::loxpKan (about 5.3 kb) (FIG. 2).

EXAMPLE 2

Selection of Strains Containing Chromosomal DNAs with Inactivated metJ Gene Fragments After the pT7ΔmetJ::loxpKan recombinant plasmids were transformed into NM522, the obtained transformants were smeared onto solid media containing carbenicillin and kanamycin (50 mg/L and 25 mg/L, respectively) and cultured at 32° C. overnight. Colonies grown on the solid media were inoculated by a tooth pick onto 3 mL of liquid media containing carbenicillin and kanamycin and cultured overnight with shaking at 250 rpm. Then, plasmid DNAs were extracted using a QIAGEN mini prep kit. After the sizes of the plasmid DNAs were determined by restriction enzyme cleavage, the plasmid DNAs were digested with restriction enzyme Pvu II and DNA fragments of about 2.4 kb (ΔmetJ::loxpKan) were resolved on 0.7% agarose gel (FIG. 2). The DNA fragments (ΔmetJ::loxpKan) were transformed into the threonine-producing strains of the pGmTN-PPC12, and the obtained transformants were smeared onto solid media containing kanamycin to select colonies. Finally, recombinant strains containing inactivated metJ genes were selected from the colonies.

EXAMPLE 3

Comparison of Threonine Productivity in Flask Cultivation Between Selected Recombinant Strains and Parent Strains Among the colonies selected after smearing on the solid media containing kanamycin in Example 2, 30 colonies were cultured in Erlenmeyer flasks containing threonine production media with the media composition of Table 1 below, and the production of threonine was evaluated.

TABLE 1

| Media composition for threonine production | |
|---|---|
| Composition | Concentration (g/L) |
| Glucose | 70 |
| Ammonium sulfate | 28 |
| $KH_2PO_4$ | 1.0 |
| $MgSO_4.7H_2O$ | 0.5 |
| $FeSO_4.7H_2O$ | 5 |
| $MnSO_4.8H_2O$ | 5 |
| Calcium carbonate | 30 |
| L-methionine | 0.15 |
| Yeast extract | 2 |
| pH (7.0) | |

First, the 30 single colonies were cultured overnight in a 32° C. incubator containing LB solid media. Then, one loopful of each of the single colonies was inoculated on 25 ml of the threonine production media and cultured for 48 hours at 32° C. with shaking at 250 rpm. The evaluation results are presented in Table 2 below. As shown in Table 2, among the 30 colonies, 25 colonies produced 24 g/L or more of threonine. On the other hand, the parent strains pGmTN-PPC12 produced 23 g/L of threonine in cultures. As seen from the above results, the recombinant strains according to the present invention exhibited excellent threonine production capability, relative to the parent strains.

Actually, the recombinant strains according to the present invention exhibited enhancement in yield of about 8% maximum, relative to the parent strains. Based on the above results, among the recombinant strains, one strain with the highest threonine productivity was selected. The selected strain was designated as E. coli FTR1221 and deposited in the Korean Culture Center of Microorganisms on Jun. 25, 2002 (accession number: KCCM-10392).

TABLE 2

| Results of flask titer test for recombinant strains | | | | |
|---|---|---|---|---|
| | Concentration of threonine (g/L) | | | |
| | 20–23 | 23–23.5 | 24 | More than 24 |
| Numbers of colonies | 2 | 3 | 10 | 15 |

EXAMPLE 4

Identification of Inactivated metJ Gene Using Southern Blotting Analysis

In order to determine whether metJ genes had been specifically inserted into the selected strains in Example 2, a southern blotting analysis was carried out. The parent strain pGmTN-PPC12 and the *E coli* FTR1221 (accession number: KCCM-10392) were cultured in 3 ml of liquid media containing kanamycin overnight with shaking at 200 rpm and then respective chromosomal DNAs were isolated using a QIAGEN chromosome kit 20. The chromosomal DNAs were digested with restriction enzyme Mlu I overnight and then size-fractionated by 0.7% agarose gel electrophoresis After the electrophoresis, the DNA fractions were transferred from the agarose gel to a nylon membrane (YOUNG Sci. Biodyne B Membrane) using a capillary transfer method [Sambrook et at, *Molecular Cloning*, vol. 1, pp. 7.46–7.48]. The membrane was dried, followed by fixation of the DNA fractions to the membrane with UV irradiation (120 mJ/cm$^2$, SpectroLinker™). The membrane was placed in a prehybridization solution 1 (Roche #1093657) at 55° C. for 2 hours for prehybridization. Then, denatured DNA probes were added to the prehybridization solution and the resultant solution was incubated in a 55° C. hybridization oven (BAMBINO 230300) overnight for hybridization.

The probes as used herein were prepared as follows. Plasmid pUG6 isolated by QIAGEN kit was digested with restriction enzymes Hinc II and EcoR V to obtain a kanamycin resistance gene fragment (about 1.7 kb) containing a loxP site. The gene fragment was heated in 100° C. water for 5 minutes and then immediately cooled on an ice for 5 minutes to obtain single-stranded DNAs. The single-stranded DNAs were incubated using a DIG Labelling and Detection kit (Roche #1093657) at 37° C. overnight. As a result, the DNA probes labeled with digoxigenin (DIG)-UDPs were obtained.

After the hybridization, DNAs nonspecifically bound to the membrane were removed using washing solutions I and II (Roche #1093657). The membrane was masked at room temperature for 30 minutes using a prehybridization solution 2 (Roche #1093657). Then, anti-DIG antibodies capable of specifically bindding to the DIG-UTPs were added and incubated at room temperature for 30 minutes. The anti-DIG antibodies nonspecifically bound to the membrane were removed using a washing solution III (Roche #1093657), and color reaction was carried out at room temperature using a Labeling and Detection kit (Roche #1093657) until bands were visualized. The results are shown in FIG. 3. No bands were observed in the parent strain pGmTN-PPC12 (lane 2) containing no kanamycin gene. On the other hand, as expected, about 1.3 kb band was observed in the *E. coli* FTR1221 (accession number: KCCM-10392) (lane 3). The 1.3 kb band represents two fragments of a part of the metJ gene (1.5 kb) and the kanamycin resistance gene (about 0.8 kb). Land 1 is a size marker.

EXAMPLE 5

Comparison of Threonine Productivity Using Fermenter

Threonine productivity in a 5 L fermenter was evaluated using the *E. coli* FTR1221 (accession number: KCCM-10392) and the parent strain pGmTN-PPC12. The media composition for initial culture is presented in Table 3 below. LB media containing 10 g/L of glucose and 0.1 g/L of L-methionine were used as seed culture media. An initial inoculation volume was adjusted to 3 to 5% of an initial culture volume in the fermenter. Glucose was six times added to fermentation media to maintain residual glucose in the media to a level of 5%. The addition of glucose was carried out when glucose was depleted. Further, during the addition of glucose, potassium monophosphate ($KH_2PO_4$) was added so that the content of the $KH_2PO4$ reached 1 wt %. An initial culture volume was 1.5 L and a final culture volume was 3.0 L. After the fermentation, the total content of glucose added was 250 g/L. A shaking speed was set at 700 to 1,000 rpm. pH and temperature were respectively set at 7.0 and 32° C. During the fermentation, pH was controlled using 25 to 28% aqueous ammonia. An aeration rate was set at 0.5 vvm.

The results are presented in Table 4 below. The parent strain produced 93.5 g/L of threonine and exhibited 37.4% of yield, i.e., the amount of threonine produced per glucose consumed. On the other hand, the *E. coli* FTR1221 produced 105 g/L of threonine and exhibited 42% of yield. Consequently, in the *E. coli* FTR1221, threonine was yielded at an increased level of 4.6%, compared to the parent strain.

TABLE 3

Initial media composition in 5-liter fermenter

| Composition | Concentration (per liter) |
|---|---|
| Glucose | 50 g |
| $KH_2PO_4$ | 4 g |
| $(NH_4)_2SO_4$ | 6 g |
| Yeast extract | 3 g |
| $MgSO_4.7H_2O$ | 2 g |
| L-methionine | 1 g |
| $FeSO_4.7H_2O$ | 40 mg |
| $MnSO_4.8H_2O$ | 10 mg |
| $CaCl_2.2H_2O$ | 40 mg |
| $CoCl_2.6H_2O$ | 4 mg |
| $H_3BO_3$ | 5 mg |
| $Na_2MoO_4.2H_2O$ | 2 mg |
| $ZnSO_4.7H_2O$ | 2 mg |
| pH (7.0) | |

TABLE 4

Results of threonine production in 5-liter fermenter by recombinant strains

| Strain | Concentration of threonine (g/L) | Fermentation duration (hr) | Yield (%) |
|---|---|---|---|
| pGmTN-PPC12 | 93.5 | 78 | 37.4 |
| FTR1221 | 105 | 96 | 42 |

As is apparent from the above description, the *E. coli* strain according to the present invention contains chromosomal DNA with inactivated metJ gene. Therefore, expression repression of threonine biosynthesis genes by a metJ gene product is prevented, thereby producing a high concentration of threonine. Furthermore, according to the L-threonine production method of the present invention, a high concentration of L-threonine can be produced in high yield.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An *Escherichia coli* strain comprising endogenous-chromosomal DNA comprising an inactivated endogenous metJ gene, wherein the *Escherichia coli* strain is resistant to α-amino-β-hydroxy valeric acid, S-(2-aminoethyl)-L-cysteine, α-amino-butyric acid, and ethionine, and wherein the *Escherichia coli* strain is capable of producing L-threonine.

2. *Escherichia coli* FTR1221 of Accession No. KCCM-10392.

3. A method of producing L-threonine comprising:
(a) culturing an *Escherichia coli* strain comprising chromosomal DNA comprising an inactivated endogenous metJ gene, wherein the *Escherichia coli* strain is resistant to α-amino-β-hydroxy valeric acid, S-(2-aminoethyl)-L-cysteine, α-amino-butyric acid, and ethionine, and wherein the *Escherichia coli* strain is capable of producing L-threonine; and
(b) recovering L-threonine from the culture.

4. A method for producing L-threonine comprising:
(a) culturing *Escherichia coli* FTR1221 of Accession No. KCCM-10392; and
(b) recovering L-threonine from the culture.

* * * * *